(12) United States Patent
Trezon

(10) Patent No.: US 7,996,994 B2
(45) Date of Patent: Aug. 16, 2011

(54) SHAVING DEVICE

(75) Inventor: Michel Trezon, Paris (FR)

(73) Assignee: Societe BIC, Clichy Cedex (FR)

( * ) Notice: Subject to any disclaimer, the term of this patent is extended or adjusted under 35 U.S.C. 154(b) by 701 days.

(21) Appl. No.: 11/909,456

(22) PCT Filed: Mar. 21, 2006

(86) PCT No.: PCT/FR2006/000629
§ 371 (c)(1),
(2), (4) Date: Jan. 16, 2008

(87) PCT Pub. No.: WO2006/100383
PCT Pub. Date: Sep. 28, 2006

(65) Prior Publication Data
US 2009/0000123 A1    Jan. 1, 2009

(30) Foreign Application Priority Data

Mar. 21, 2005 (FR) ..................... 05 02737

(51) Int. Cl.
*B26B 21/40* (2006.01)
*A61B 18/14* (2006.01)
(52) U.S. Cl. .................. 30/34.05; 219/223; 606/36
(58) Field of Classification Search ........... 30/32, 34.05, 30/140; 219/222, 223; 606/36, 43, 133
See application file for complete search history.

(56) References Cited

U.S. PATENT DOCUMENTS

| | | | | |
|---|---|---|---|---|
| 2,231,219 A | * | 2/1941 | Peterson | 219/223 |
| 2,727,132 A | * | 12/1955 | Hills | 219/223 |
| 2,888,927 A | | 6/1959 | Fozard | |
| 3,197,612 A | * | 7/1965 | Reich | 219/223 |
| 3,934,115 A | * | 1/1976 | Peterson | 219/223 |
| 4,237,886 A | | 12/1980 | Sakurada et al. | |
| 5,026,369 A | | 6/1991 | Cole et al. | |
| 5,065,515 A | * | 11/1991 | Iderosa | 30/140 |
| 5,182,857 A | * | 2/1993 | Simon | 30/34.05 |
| 5,221,280 A | | 6/1993 | Gross et al. | |
| 5,287,294 A | | 2/1994 | Baert et al. | |
| 5,364,394 A | | 11/1994 | Mehl | |
| 5,419,344 A | | 5/1995 | DeWitt | |
| 5,470,332 A | | 11/1995 | Mehl, Sr. et al. | |
| 5,534,003 A | | 7/1996 | Cole | |
| 5,606,798 A | * | 3/1997 | Kelman | 30/41.5 |

(Continued)

FOREIGN PATENT DOCUMENTS

FR        1327344        5/1963

(Continued)

OTHER PUBLICATIONS

International Search Report for International Application No. PCT/FR2006/000629, mailed Aug. 2. 2006, French language version.

(Continued)

*Primary Examiner* — Hwei-Siu C Payer
(74) *Attorney, Agent, or Firm* — Jones Day

(57) ABSTRACT

A manual shaving device that includes a support having at least one razor blade designed to cut a hair as it passes over it mounted thereon and at least one conducting member designed to transmit an electric current to a root of the hair as it passes over it, the electric current being designed to damage a follicle of the hair by electrolysis.

25 Claims, 6 Drawing Sheets

U.S. PATENT DOCUMENTS

| | | | |
|---|---|---|---|
| 5,778,535 A * | 7/1998 | Ledesma | 30/50 |
| 5,797,926 A | 8/1998 | Mehl, Sr. | |
| 5,833,687 A | 11/1998 | Mehl, Sr. et al. | |
| 5,846,252 A | 12/1998 | Mehl, Sr. | |
| 5,868,738 A | 2/1999 | Mehl, Sr. | |
| 6,014,918 A | 1/2000 | Orloff et al. | |
| 6,063,076 A | 5/2000 | Mehl, Sr. et al. | |
| 6,158,126 A * | 12/2000 | Rose et al. | 30/43.92 |
| 6,159,222 A | 12/2000 | Yiu | |
| 6,533,775 B1 * | 3/2003 | Rizoiu | 606/9 |
| 6,544,259 B1 | 4/2003 | Tsaliovich | |
| 6,620,158 B2 | 9/2003 | Ronci | |
| 6,817,101 B1 * | 11/2004 | Bohmer | 30/34.05 |
| 6,825,445 B2 * | 11/2004 | Shalev et al. | 219/223 |
| 6,836,966 B2 * | 1/2005 | Patrick | 30/34.05 |
| 7,170,034 B2 * | 1/2007 | Shalev et al. | 219/223 |
| 7,479,137 B2 * | 1/2009 | Yamazaki et al. | 606/9 |
| 2003/0125754 A1 * | 7/2003 | Davis et al. | 606/133 |
| 2007/0239152 A1 * | 10/2007 | Trezon | 606/36 |
| 2007/0271714 A1 * | 11/2007 | Adam et al. | 15/22.2 |
| 2009/0000123 A1 * | 1/2009 | Trezon | 30/34.1 |
| 2009/0211101 A1 * | 8/2009 | Azar et al. | 30/41.6 |
| 2009/0287208 A1 * | 11/2009 | Rosemberg | 606/36 |
| 2010/0024615 A1 * | 2/2010 | Rebaudieres et al. | 83/14 |

FOREIGN PATENT DOCUMENTS

| | | |
|---|---|---|
| FR | 2 383 675 | 10/1978 |
| GB | 2 392 091 | 2/2004 |
| WO | WO 95/17856 | 7/1995 |
| WO | WO 00/57803 | 10/2000 |

OTHER PUBLICATIONS

International Search Report for International Application No. PCT/FR2006/000629, mailed Aug. 2, 2006, English translation of French version.

* cited by examiner

SHAVING DEVICE

CROSS-REFERENCE TO RELATED APPLICATIONS

This application is a national stage application of International Application No. PCT/FR2006/000629, filed on Mar. 21, 2006, which claims the benefit of French Patent Application No. 0502737, filed on Mar. 21, 2005, the entire contents both of which are incorporated herein by reference.

BACKGROUND OF THE INVENTION

1. Field of the Invention

Embodiments of the present invention relate to a device that makes it possible, simultaneously while shaving by hand, to cut hair and to damage, or even destroy, the hair follicle.

2. Description of the Related Art

Conventional manual shavers generally use one or more blades that exclusively cut hair. They do not prevent hair regrowth because they do not act on the roots.

Accordingly, it is an object of embodiments of the present invention to remedy this disadvantage of conventional shavers.

SUMMARY OF THE INVENTION

To this end, embodiments of the present invention are directed to a manual shaving device comprising a support on which at least one razor blade designed to cut a hair as it passes over it, is mounted. Embodiments of the present invention further comprise at least one conducting member designed to transmit an electric current to the root of a hair as it passes over it, the electric current being designed to damage the follicle of the hair by electrolysis.

The method according to embodiments of the invention comprises, while moving the razor over the area that is to be depilated, sending an electrical electrolysis current into the hair in order to reach its papilla and its root, just before it is cut with the blade. Embodiments of the present invention also relate to an aesthetic method of shaving aimed at delaying the regrowth of the shaved hairs, for which at least one razor blade and at least one conducting member are provided, and in which a shaving operation involves moving the at least one blade over the skin in such a way so as to shave the hairs in a given area and, at the same time, moving the at least one contact member over the skin in contact therewith, together with supplying an electrical current to the conducting member such that, as the shaving device is moved over the skin, an electric current is transmitted to the follicles of the hair in at least part of the shaved area in order to damage the follicles by electrolysis.

Because of this simultaneous method, the root of the hair or follicle is damaged, or even destroyed following repeated use of the device, resulting in the hair being removed and its regrowth being considerably delayed.

One embodiment of a device for implementing this method comprises a blade support. This blade support includes a conducting element having two conducting members positioned in front of and behind the razor blades, that apply an electrical current. Thus, when a user moves the device over the area that is to be shaved or epilated, the front conducting member, which is connected to an internal generator, is the first to slide over the hair and, by contact, transmits the current and the hair. The blades then pass over the hair and cut it.

In some embodiments of the present shaving device, the blade support is preferably removably positioned on or attached to a housing. In addition, the at least one conducting member is a positive conducting member and is offset relative to the at least one razor blade in the direction of travel thereof, and is preferably provided in front of the at least one blade in its direction of travel. Further, the device also includes a casing that comprises, on its exterior wall and preferably in a region for holding the latter, a contact element providing a current return path, where the contact element is negatively connected and is preferably in the form of a metal sheet.

The conducting element comprises a first conducting member and a second conducting member where the at least one razor blade is positioned between the first conducting member and the second conducting member in the direction of travel of said blade.

The first conducting member which is positive, is positioned in front of the at least one blade with respect to its direction of travel and the second conducting member, which is negative, is positioned behind the at least one blade, where the first and second conducting members are positioned parallel to one another and preferably parallel to the at least one razor blade. The conducting members are in the form of a pad, preferably made of a metal sheet. The conducting members have current supplied to them by permanent contact with at least one contact hook that is preferably elastically displaceable.

The casing comprises an internal electrical generator electrically connected to the conducting members.

In addition, in another embodiment of the present invention, a plurality of razor blades positioned parallel to one another are provided. The device also includes a blade support that comprises two conducting pads, a positively connected front pad for transmitting the current and a negatively connected rear pad for the current return path. The blade support may also comprise only the positively connected front pad. In such case, the current return path is provided by a negatively connected metal part that is fixed to the exterior face of the casing, so as to be in contact with the hand. In both instances, the resistance of the body is at the same potential as the internal generator and the current that produces the electrolysis phenomenon circulates perfectly.

Now turning to the shaving operation, the operation comprises: providing a casing, that supports at least one blade and the at least one conducting element, the casing having a region for holding; moving the at least one blade and the at least one conducting element by hand by the user; providing a current-conducting means, in contact with the user so as to provide a current return path for the current transmitted by the at least one conducting element; and moving the at least one blade with respect to the movement of the at least one conducting member in such a way so as to transmit the electric current to the root of a given hair before that given hair is cut by the blade.

The shaving operation may be repeated periodically, and preferably daily in the case of beard growth and weekly in the case of hair on other parts of the body, until the follicles of most of the treated hairs have been destroyed. It is thus possible to obtain a result which, aesthetically and in terms of how well it lasts, is similar to that of conventional epilation.

Other features and advantages of embodiments of the present invention will become apparent in the course of the description that follows, which is given by way of nonlimiting examples with reference to the included drawings.

DESCRIPTION

In the following description, identical references have been maintained in the various figures to denote elements that are identical or similar.

Figure 1:
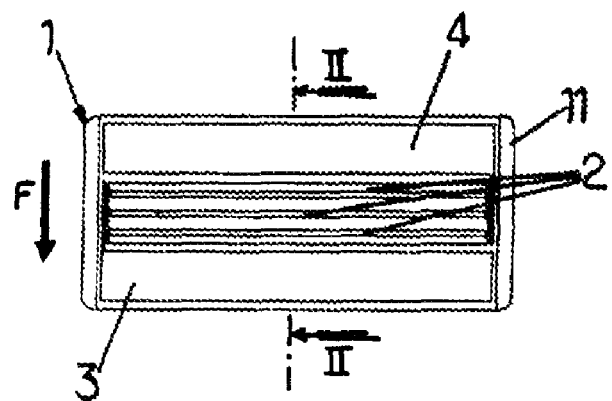
FIG. 1 is a plan view of a blade support, according to a first embodiment of the present invention.
Figure 2:
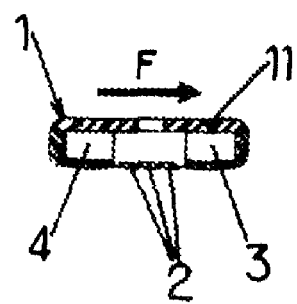
FIG. 2 is a cross-sectional view take about line II-II in FIG. 1.
Figure 4:
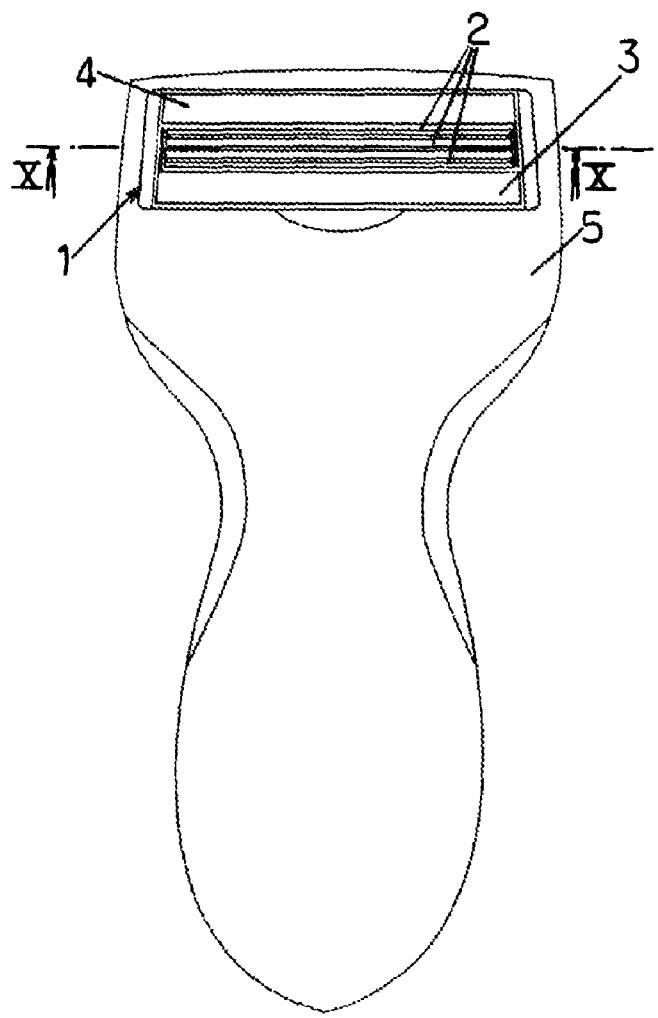
FIG. 4 is a front view of a shaving device comprising the blade support depicted in FIG. 1, according to the one embodiment of the present invention.

With reference to FIGS. 1 and 2, an embodiment of the present device comprises a blade support 1 that is attached to the casing 5 of the shaving device as depicted in FIG. 4. This blade support 1 is equipped with a conducting element comprising two conducting members or pads (3, 4) aligned parallel to each other. A positive conducting pad 3 is positioned at the front of the blade support 1 and a negative conducting pad 4 that forms the current return path, is positioned at the rear of the blade support 1, these pads being separated by the razor blades 2. The front and the rear of the blade support 1 are defined by the direction of travel of the blades 2, as indicated by arrow F in FIG. 1. However, this layout of the pads is not essential. For example, in the case of a dry razor in which the blades are electrically driven behind a grating, there is no one single direction of travel for cutting the hairs, unlike the case of razor blades of the wet razor type, which have been depicted by way of example.

Figure 6:
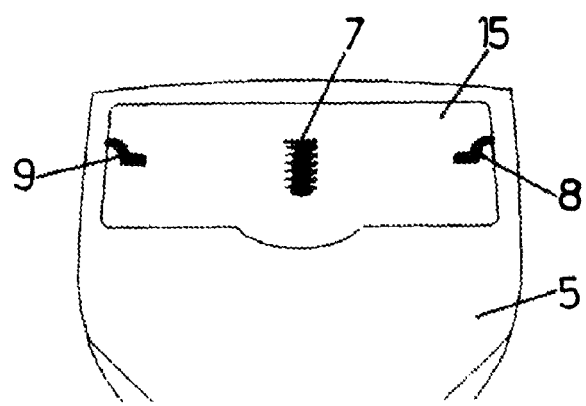
FIG. 6 is a partial plan view of a shaving device without the blade support, according to an embodiment of the present invention.

FIG. 6 depicts, in a front view, a housing 15 of the casing 5 for attaching the blade support 1 to the casing 5. This housing 15 comprises, in the middle, a pivot pin 7 equipped with a spring and, at its ends, two contact hooks (8, 9) that are used to hold the blade support 1 and establish electrical connection with each of the pads (3, 4).

Figure 7:
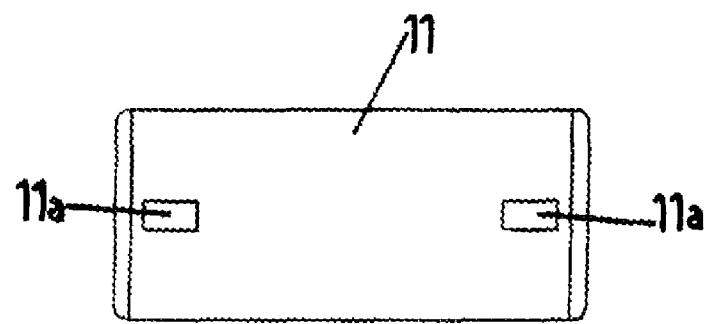
FIG. 7 is a top view of a blade support element, according to an embodiment of the present invention.

FIG. 7 illustrates a top view of element 11 that forms the framework of the blade support 1. Element 11 has aligned cut-outs 11a in the middle of each end through which the corresponding contact hooks (8, 9) pass. The contact hooks (8, 9) are mounted such that they can pivot and are elastically returnable to the engaged position so as to removably attach the blade support 1 to the housing 15 as can be seen clearly in FIG. 10.

It will be clear to persons skilled in the art on studying these figures that the blade support 1 forms a removable and disposable shaver cartridge that can be held in place by other types of fastening means or devices and which can also possibly be connected to the casing using an articulated joint, as is well known in the case of razors for wet shaving.

Figure 8:
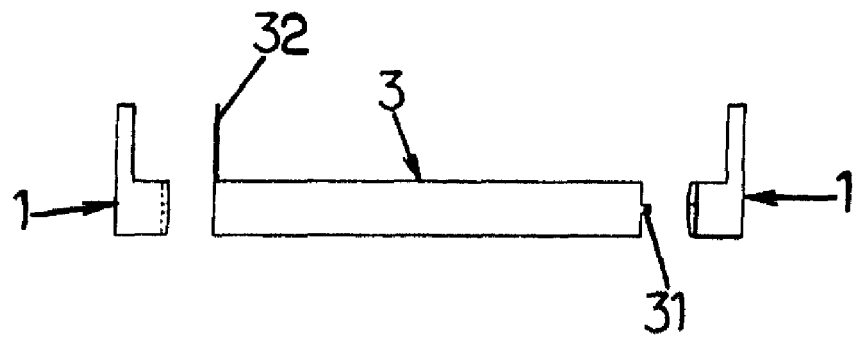
FIGS. 8 and 9 are front and side views of blade support conducting members, according to an embodiment of the present invention.
Figure 9:
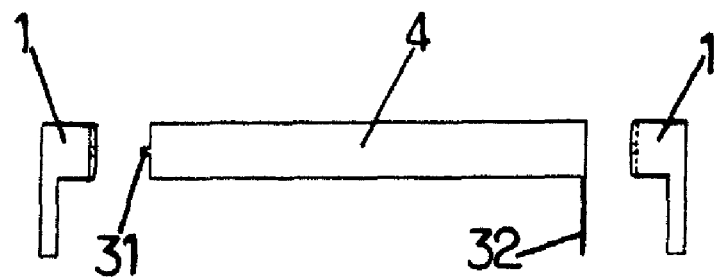

FIGS. 8 and 9 provide further details on the conducting pads (3, 4). The conducting pads (3, 4) are identical and positioned in opposition on the blade support 1. With reference to FIG. 4, the pads (3, 4) consist of a slim metal plate. As shown in FIG. 8, a centered peg 31 at one end provides for attachment to the blade support 1. Part 32, which is bent at a right angle at the end opposite to where peg 31 is located, is positioned near the cut-out in the blade support 1, in order to provide the electrical connection with the contact hook 8 or 9. By way of nonlimiting example, the pads (3, 4) are of the order of approximately 35 mm long and 5 mm wide.

Figure 10:
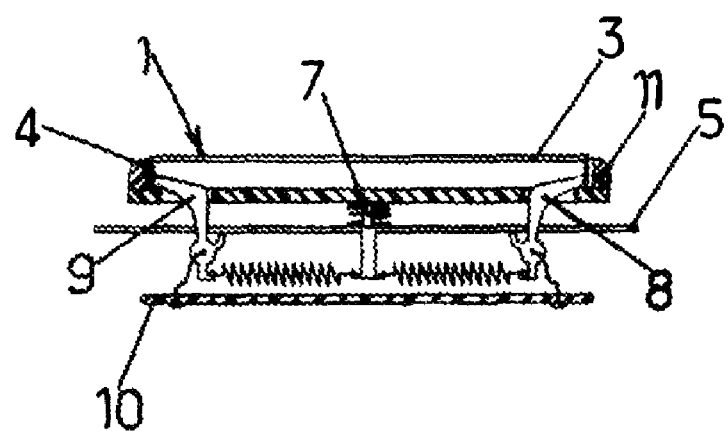
FIG. 10 is a partial cross-sectional view about line X-X in FIG. 4.

FIG. 10 depicts, in cross section, the electrical connection of the positive conducting pad 3 and negative conducting pad 4. The contact hooks (8, 9) are connected to an internal generator 10 and remain in constant contact with the corresponding pads (3, 4).

However, the conducting pads (3, 4) may adopt a great many other forms and, for example, may be more robust. They need not necessarily be made of metal either. Indeed, their purpose is to transmit current from the generator 10 to the root of the hairs through contact with the skin and, to a lesser extent, with the outside of the hairs if these hairs have not already been cut. The conducting pads (3, 4) could therefore be made of any current-conducting material. The current is therefore transmitted simply by rubbing the pads against the skin.

Figure 11:
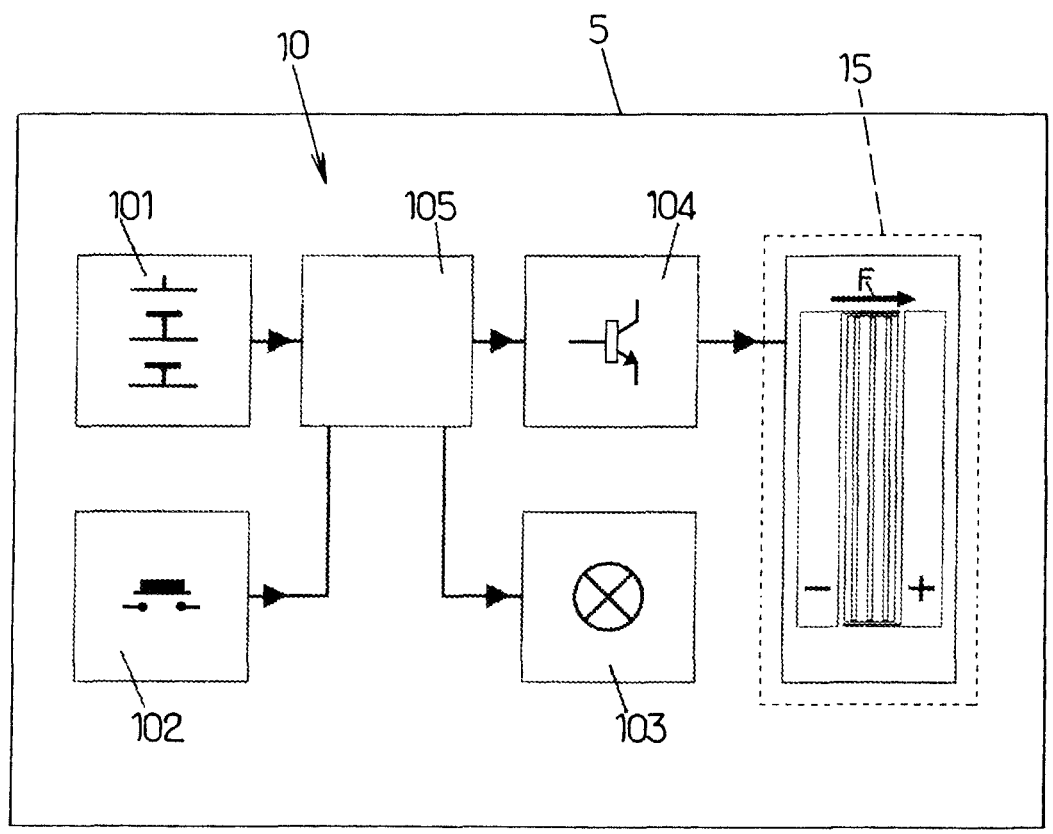
FIG. 11 is a block diagram of a blade support and the supply of electrical power thereto, according an embodiment of the present invention.

FIG. 11 is a block diagram for the mechanical and electrical systems. The electric generator 10 comprises a current source 101, here, for example, a 9-volt battery, an on/off switch 102, here, for example, in the form of a push-button, an indicator lamp 103, a regulating unit 104 that controls the current supplied to the conducting pads (3, 4) and an electric module 105 connected to its components (101-104) in order to control the operation of the shaving device.

Figure 5:
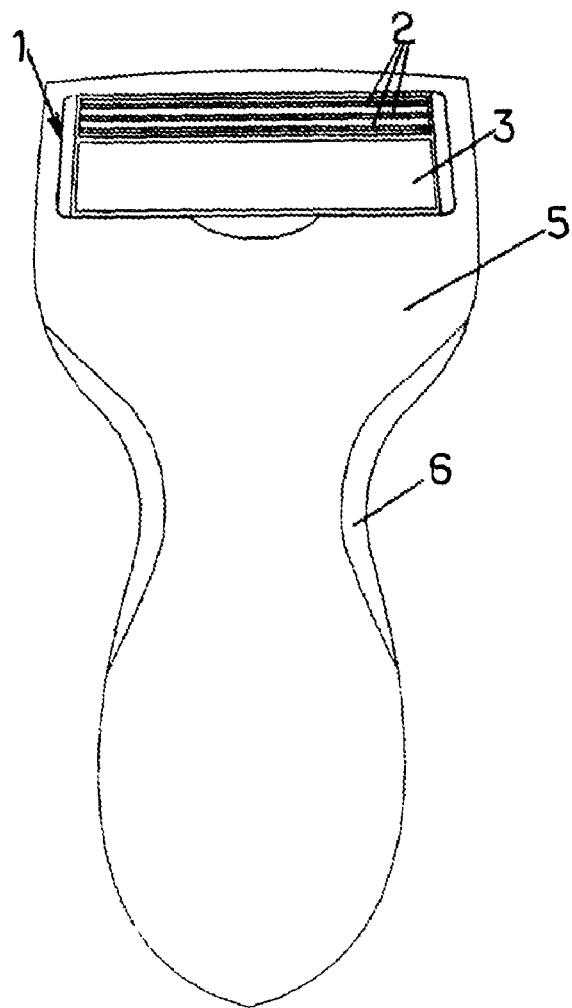
FIG. 5 is a front view of a shaving device comprising the blade support depicted in FIG. 3, according to another embodiment of the present invention.

It is advantageous for the electronic module 105 to be miniaturized and for the current source 101 to be in the form of a cell battery or a rechargeable battery, so that the entire generator 10 can be housed inside the casing 5 of the shaving device which, as can be seen in FIGS. 4 and 5, is in the form of a small hand-held device, that is almost as easy to handle as a wet razor. Indeed, according to embodiments of the present invention, the current transmitted to the roots of the hairs needs simply to be enough to begin an electrolysis phenomenon at the dermal papilla, which phenomenon is a known phenomenon per se. However, unlike electrolysis epilation devices that require a current to be applied to the root of each hair for several tens of seconds, or even for several minutes, the amounts of electrical energy used by the invention in a given area are very small. Nevertheless, it has been found that, in spite of the small amount of current transmitted to each hair as a result of the conducting pads passing quickly over the skin as the present bladed shaver device is handled in the usual way, the hair follicles are damaged, thus delaying hair regrowth.

It is preferable to position the positive conducting pad 3 first, in the direction of travel of the razor, so that the hair can be electrolyzed before it is cut.

Figure 3:
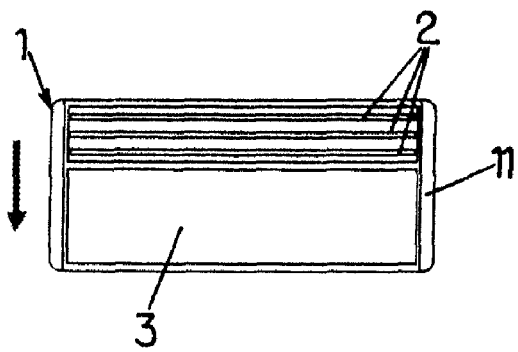
FIG. 3 is a top plan view of a blade support, according to another embodiment of the present invention.

According to an alternative embodiment of the present invention illustrated in FIG. 3, the blade support 1 is equipped with razor blades 2 positioned at the rear, but over a greater width at the front, there is only the positive conducting pad 3. In this case, FIG. 5 shows that a metal sheet 6, fixed externally to the casing 5, is entirely able to provide the negative contact for the current return path. This sheet 6 forms a contact element, the purpose of which is identical to the purpose of the second conducting member or pad 4 in the first embodiment. These two types of conducting means (4, 6) are able, with the first conducting member or pad 3, to produce a fairly large current-circulation loop.

It is, however, perfectly conceivable for the conducting pad or pads in contact with the skin and the hair to be connected to the negative terminal of the current generator 10. Furthermore, embodiments of the present invention do not exclude a ground-return path for the current with a suitable generator, for example, when the shaver is being used in the shower. Indeed, the voltages needed to obtain the electrolysis phenomenon are very low, in the order of 30 volts, and the currents are very weak at just a few milliamps. Thus, there is therefore no risk of electrocution using the shaving device produced according to the present invention. Furthermore, it is entirely possible to disconnect the conducting members or pads (3, 4), which are removably mounted, from the blade support 1, for example, by positioning these members on the casing 5 near the housing 15 so that they come into contact with the skin.

In the light of the foregoing description it will become apparent that the shaving method comprising shaving with the blades in the usual way, sliding the cutting edge of these blades over the skin, in the case of a wet razor, or sliding a grating over the skin, in the case of a dry razor, while at the same time applying an electrical current to the skin surface and hence the hairs via the conducting pads (3, 4) or any other conducting means or member, in order to generate the electrolysis phenomenon.

By repeating the shaving operation using the device described hereinabove, it is possible, after a certain number of uses separated by some period of time, to destroy the dermal papilla. What this means is that not only is the regrowth of the hair delayed, but its regrowth is temporarily halted similar to that obtained using conventional epilation methods with wax or the like. However, an advantage of the present invention and method is that this result can be obtained without the user having to change his or her shaving habits. Repeated application of the current for electrolysis during daily shaving of the beard area makes it possible to practically destroy the roots. Likewise, a weekly shaving operation, for example of the legs, the bikini line or the armpits, leads to very severe damage to the dermal papilla after a few weekly shaving operations, having very significant effect on hair regrowth.

The invention claimed is:

1. A manual shaving device comprising:
   a casing;
   a support disposed on the casing and having at least one razor blade designed to cut a hair as it passes over it mounted thereon;
   at least one conducting element designed to transmit an electric current to a root of a hair as it passes over it, the electric current being designed to damage a follicle of the hair by electrolysis; and
   a contact element disposed on an external wall of the casing, providing a current return path.

2. The manual shaving device according to claim 1, wherein the contact element is located in a region for holding the casing.

3. The manual shaving device according to claim 1, wherein the at least one conducting element is offset relative to the at least one razor blade in a direction of travel thereof, in front of the at least one blade relative to the direction of travel.

4. The manual shaving device according to claim 1, wherein the at least one conducting element is positioned in front of the at least one razor blade relative to a direction of travel of the at least one blade.

5. The manual shaving device according to claim 1, wherein the at least one conducting element comprises a first conducting element and a second conducting element.

6. The manual shaving device according to claim 5, wherein the at least one razor blade is positioned between the first conducting member and the second conducting member.

7. The manual shaving device according to claim 1, wherein the casing comprises an internal electrical generator electrically connected to the at least one conducting member.

8. A manual shaving device comprising:
   a support having at least one razor blade designed to cut a hair as it passes over it mounted thereon; and
   at least one conducting element designed to transmit an electric current to a root of the hair as it passes over it, the electric current being designed to damage a follicle of the hair by electrolysis.

9. The manual shaving device according to claim 8, wherein the at least one conducting element is offset relative to the at least one razor blade in a direction of travel thereof, in front of the at least one blade relative to the direction of travel.

10. The manual shaving device according to claim 8, wherein the at least one conducting element is a positive conducting element positioned in front of the at least one blade relative to a direction of travel of the at least one blade.

11. The manual shaving device according to claim 8, wherein the support is disposed on a casing, the casing comprising, on an exterior wall thereof, and in a region for holding the casing, a contact element providing a current return path.

12. The manual shaving device according to claim 11, wherein the contact element is negatively connected and is in the form of a metal sheet.

13. The manual shaving device according to claim 11, wherein the casing comprises an internal electrical generator electrically connected to the at least one conducting member.

14. The manual shaving device according to claim 8, wherein the at least one conducting element comprises a first conducting member and a second conducting member.

15. The manual shaving device according to claim 14, wherein the at least one razor blade is positioned between the first conducting member and the second conducting member.

16. The manual shaving device according to claim 14, wherein the first conducting member positioned in front of the at least one blade is positive and the second conducting member positioned behind the at least one blade is negative.

17. The manual shaving device according to claim 8, wherein the at least one conducting element is in the form of a pad formed of a metal plate.

18. The manual shaving device according to claim 8, wherein the at least one conducting element has current supplied to it through permanent contact with at least one contact hook that is elastically displaceable.

19. The manual shaving device according to claim 8, wherein the support comprises a plurality of razor blades positioned parallel to one another.

20. A method of shaving to delay the regrowth of shaved hairs, the method comprising the steps of:
   providing a manual shaving device comprising:
      a support having at least one razor blade designed to cut a hair as it passes over it mounted thereon; and
      at least one conducting element designed to transmit an electric current to a root of the hair as it passes over it; and
   performing a shaving operation comprising the steps of:
      moving the manual shaving device over the skin so as to shave the hairs in a given area; and, at the same time supplying an electrical current to the at least conducting element so that as the manual shaving device is moved around, an electric current is transmitted to follicles of the hairs in at least part of the given area thereby damaging the follicles by electrolysis.

21. The method according to claim 20, wherein during the shaving operation, the at least one blade is moved with respect to the movement of the at least one conducting element such that the electric current is transmitted to a root of a given hair before that given hair is cut by the blade.

22. The method according to claim 20, wherein the manual shaving device further comprises a casing for supporting the at least one blade and the at least one conducting element, the casing having a region for holding.

23. The method according to claim 22, wherein movement of the manual shaving device is performed by hand by a user.

24. The method according to claim 20, wherein the manual shaving device further comprises a current conducting means, wherein the current conducting means is in contact with a user so as to provide a current return path for the current transmitted by the at least one conducting element.

25. The method according to claim 20, wherein the shaving operation is repeated periodically until the follicles of most of the treated hairs have been destroyed.

* * * * *